United States Patent [19]

Hermolin et al.

[11] Patent Number: 4,709,100

[45] Date of Patent: Nov. 24, 1987

[54] PROCESS FOR THE MANUFACTURE OF MIXTURES OF 3-PHENOXYBENZYL BROMIDE AND 3-PHENOXYBENZAL BROMIDE

[75] Inventors: Joshua Hermolin, Ramat Hasharon; Arieh Kampf, Meitar, both of Israel

[73] Assignee: Bromine Compounds Ltd., Beer-Sheva, Israel

[21] Appl. No.: 837,769

[22] Filed: Mar. 10, 1986

[30] Foreign Application Priority Data

Apr. 1, 1985 [IL] Israel ......................................... 74775

[51] Int. Cl.$^4$ ........................ C07C 41/22; C07G 13/00
[52] U.S. Cl. ................................. 568/639; 204/157.92
[58] Field of Search ......................... 568/639; 570/191; 204/157.92

[56] References Cited

U.S. PATENT DOCUMENTS 4,108,904  8/1978  Brown et al. ................... 568/639 X

FOREIGN PATENT DOCUMENTS 633765  12/1982  Switzerland .

OTHER PUBLICATIONS

Fieser & Fieser, Reagents for Organic Synthesis, (1967) 208.

Maerky, Chemical Abstracts, vol. 98 (1983) 160386g.

*Primary Examiner*—J. E. Evans
*Attorney, Agent, or Firm*—Schwartz, Jeffery, Schwaab, Mack, Blumenthal & Evans

[57] ABSTRACT

The present invention relates to a process for the manufacture of mixtures of 3-phenoxybenzyl bromide and 3-pnenoxybenzal bromide using dibromodimethylhydantoin as brominating agent. According to the process, the reaction between the m-phenoxytoluene and the brominating agent is carried out in a non-polar solvent at temperatures above 65 degrees C. The molar ratio between the reactants is selected in the range of between 0.5:1 to 1.25:1 of the brominating agent towards the 3-phenoxytoluene. In a preferred embodiment, a radical initiator is incorporated being selected from the group consisting of ultraviolet rays and compounds containing azo-groups, peroxides or mixtures thereof. According to a most preferred embodiment the addition of the free radical and of the brominating agent is carried out gradually. The process is characterized by its very high yield, the products obtained being of a very high quality.

11 Claims, No Drawings

PROCESS FOR THE MANUFACTURE OF MIXTURES OF 3-PHENOXYBENZYL BROMIDE AND 3-PHENOXYBENZAL BROMIDE

The present invention relates to a process for the manufacture of mixtures of 3-phenoxybenzyl bromide (hereafter referred to as PBZYB) and 3-phenoxybenzal bromide (hereafter referred to as PBZAB). More particularly the invention relates to a method for the manufacture of mixtures of PBZYB and PBZAB, containing a minimum amount of by-products.

As known, mixtures of PBZYB and PBZAB are important intermediates for the syntheses of synthetic pyrethroid-type insecticides.

It has been reported, that the process of brominating the side chain of m-phenoxytoluene, by using molecular bromine as the brominating agent, is usually accompanied by ring bromination.

The production of aromatic nucleus brominated compounds causes a reduction of the yield, and involves industrial troubles due to difficulty of separating the by-products from the side chain brominated compounds as the desired product.

Various improvements dealing with the problem of preparing mixtures of brominated compounds, in which only the side chain is brominated, are claimed in a large number of patents. Thus, according to U.S. Pat. No. 4,014,940 the bromination of the side chain of m-phenoxytoluene with bromine is carried out at a temperature of 220 degrees Celsius in the presence of phosphorus halide. A slight modification is claimed in the U.S. Pat. No. 4,010,087 wherein radiation of ultraviolet rays is applied during said bromination. However in both patents it is mentioned that several percentages of the aromatic nucleus-brominated compounds are present, which is indeed a clear disadvantage of the process.

According to European Patent Application No. 3380 the manufacture of mixtures of PBZYB and PBZAB is improved by using a molar excess of molecular bromine on 3-phenoxytoluene (1.3 to 1.5 moles per 1 mole), while the reaction is carried out at a temperature in the range of 195 to 235 degrees Celsius, in the presence of an inert gas and with complete absence of radiation, catalyst or added solvent. It is specifically mentioned that contact of the reactants at a lower temperature results in increased nuclear bromination, while contact at a higher temperature results in increased production of other by-products, known as "heavy ends" i.e. higher boiling materials of undetermined identity.

It is also suggested that, in order to minimize the undesirable by-products, no local excess of bromine relative to the m-phenoxytoluene should be ensured.

As mentioned therein this is achieved by a thorough mixing of the bromine with the toluene and an inert gas and by controlling the rate at which the bromine is introduced into the toluene.

In a very recent U.S. Pat. No. 4,393,246, a new process for improving the bromination of the side chain of m-phenoxytoluene is claimed. In this process the bromination is carried out with a polyhalogenated ethane in the presence of various catalysts such as activated charcoal, coke or activated carbon. The reaction temperature is in the range of 100 to 270 degrees Celsius.

Along the same approach of utilizing a brominating agent other than bromine, a process for the manufacture of phenoxybenzylidene bromide from meta-phenoxytoluene using N-Bromosuccinimide as the brominating agent is described in the German Offen. No. 2,810,305. While relatively high yields are claimed to be achieved, the process suffers from a long reaction time such as 23 hours as mentioned in the Example given in the specification.

In Swiss Pat. No. 633,765 a process is described for the manufacture of ortho-substituted benzyl and -benzal bromides from ortho-substituted toluene, said substitutients being electron withdrawing groups, using N-Bromosuccinimide and 2,4-dibromo-5,5-dimethylhydantoin as the brominating agent. The reaction is carried out at temperatures in the range of 80 to 110 degrees Celsius and in the presence of symmetric halogenated alkanes, as inert solvents, as medium of the reaction. As known from various textbooks (e.g. Free Radical chain reactions by E. S. Huyser, 1970, page 126) the relative reactivities of substituted toluenes towards bromination by N-bromosuccinimide are essentially the same as those observed from bromination with molecular bromine. With an electron-donating group an electrostatic effect will persist which will impart more activation of the side chain and thus being more likely to undergo bromination.

It is an object of the present invention to provide a simple process for the manufacture of mixtures of 3-phenoxybenzyl bromide (PBZYB) and 3-phenoxybenzal bromide (PBZAB) which is substantially free of nuclear brominated products. It is another object of the present invention to provide a simple process for the manufacture of mixtures of PBZYB and PBZAB at high yields. It is yet another object of the present invention to provide a simple process for the manufacture of mixtures of PBZYB and PBZAB which process can be easily carried out in a continuous manner. Thus the invention consists in a process for the manufacture of mixtures of PBZYB and PBZAB from 3-phenoxytoluene using dibromodimethylhydantoin as the brominating agent which is characterized by the fact that the bromination is carried out in a non-polar solvent at temperatures above 65 degrees Celsius, and using a molar ratio between dibromodimethylhydantoin to meta-phenoxytoluene in the range of 0.5:1 to 1.25:1. It was unexpectedly found that by carrying out the above reaction under said conditions, preferably in the presence of initiators, high yields of above 95% of the desired products are achieved.

Initiators are generally utilized in reactions of this type and include compounds selected from azo-groups, peroxides, ultraviolet rays, or any combination thereof. A person skilled in the art will select the proper means according to the availabilities at site as well as the goal desired to achieve at the optimal costs.

One of the advantages of the process is the very fast reaction that occurs, being generally less than thirty minutes, which is in contrast to the long reaction times encountered in the various processes suggested for the manufacture of such mixtures.

The organic solvent which is present during the reaction should be non-polar, without containing hydrogen atoms amenable to free radical reactions such as involved in the present system. Generally these are inert solvents which are selected from chlorinated and brominated hydrocarbons known in the art such as tetrachloroethane, tetrachloroethylene, tetrachloromethane, chlorobenzene etc.

The temperature for carrying out the reaction between the m-phenoxytoluene and the dibromodimethylhydantion, should be above 65 degrees centigrade and most preferably it should be selected according to the boiling point of the inert organic solvent present in the reaction system. Attempts to carry out the reaction below 65 degrees centigrade, have shown that its rate was very slow and also considerable bromination occurs on the aromatic nucleus. The latter effect has a great disadvantage to the process since, as known, in the procedures by which the mixtures of bromides are converted to the insecticidal esters, it has been found very desirable that the mixture of bromides is substantially free from nuclear brominated by-products which will correspondingly be found in the insecticidal ester product.

Dibromodimethylhydantoin offers several economical and technological advantages over other brominating agents, e.g. N-Bromosuccinimide, which was even suggested for the bromination of m-phenoxytoluene. Among these advantages the following are mentioned:

It is less voluminous (in the order of 50%).

It is more easily separated from the product mixture at the end of the reaction.

It necessitates only one recycling process per two active bromine atoms.

It is recycled at higher yields, and

It is by-far less expensive on a weight basis and on the active bromine constituent.

The process has also a clear advantage over the bromination with molecular bromine, wherein, in order to minimize the formation of undesirable by-products, it is required to ensure that no local excess of the free bromine prevail relatively to the m-phenoxytoluene and therefore, the bromine has to be introduced into the reactor carefully and slowly at a very strict controlled rate, while very vigorous mixing must be maintained.

The yields of the reaction between the m-phenoxytoluene and the dibromodimethylhydantoin are very high; after less than thirty minutes more than 90% of the desired components are obtained.

Among the suitable radical initiators, it should be mentioned the known initiators suggested for this type of reactions such as azo-bis-isobutyronitrile, benzoyl peroxyde etc. The amounts of such radical initiators are not critical and may be selected in a very broad range depending on the availability and costs. Preferably, the amount should be in a range of between 1 to 100 parts by weight per 100 parts of m-phenoxytoluene and most preferably in the range of 1 to 10 by weight initiator per 100 parts of m-phenoxytoluene.

According to a preferred embodiment, an amount of about 10% of the radical initiator is introduced from the beginning into the reactor. In this case the reaction will proceed in a smooth manner.

The process according to the present invention can be easily operated on an industrial scale. In this case it is most preferred to incorporate the reagents, dibromodimethylhydantoin and radical initiator, by gradual addition in small portions.

The reaction between m-phenoxytoluene and dibromodimethylhydantoin is conveniently carried out at atmospheric pressure, or in the usual case at the slightly elevated autogeneous pressure existent at the boiling point from the passage of the vapors out of the reactor and associated equipment. However, operation under slightly higher pressure or slightly lower pressure (i.e. under vacuum) is quite feasible, provided adequate precautions are taken to avoid possible nuclear bromination.

The amount of inert solvent to be present in the system, may be selected in a very broad range. Of course an excess of solvent will decrease the concentrations of the reactants and will increase the total reaction time. On the other hand, a too low amount of solvent might increase, to some extent, the amount of by-products resulting from undesirable side reaction during the bromination. Therefore a person skilled in the art will select the proper amount between the above two criteria. Generally the preferred amount of inert solvent should be in a range of between 50% to 90% by volume of the reactants.

Another advantage of the method according to the present invention, is the substantially absence of the m-phenoxytoluene in the final reaction mixture. This is a result of the high yield of bromination which is achieved in the system. Accordingly, the final reaction mixture of PBZYB and PBZAB is suitable, such as obtained from this method, without any further purification, as a starting material in the preparation of intermediates for the desired pyrethroid insecticides.

While the invention will now be described in connection with certain preferred embodiments in the following Examples, it will be understood that it is not intended to limit the invention to these particular embodiments. On the contrary, it is intended to cover all alternatives, modifications and equivalents as may be included within the scope of the invention as defined by the appended claims. Thus, the following Examples which include preferred embodiments will serve to illustrate the practice of this invention, it being understood that the particulars described are by way of example and for purpose of illustrative discussion of preferred embodiments of the present invention and are provided what is believed to be the most useful descriptive illustration of the invention.

In the Examples, the yield percentages given are based on the m-phenoxytoluene. Also it should be pointed out that Example 5 does not represent the present invention, being only presented for comparison purpose.

EXAMPLE 1

An amount of 600 g of m-phenoxytoluene (produced by Fluka) was introduced into a three necked flask, equipped with a stirrer and a reflux condenser. Into the same flask the following reagents were introduced:

714 g of 1,3-dibromodimethylhydantoin;

42 g of azo-iso-butyronitrile, and 6,000 cc of carbontetrachloride.

The mixture was brought to boiling by fast heating means (to about 77 degrees Celsius) and kept to this temperature for about 30 minutes. After cooling into a water bath to room temperature, under continuous stirring, the solid was filtered off, washed with two portions of carbontetrachloride (each of 100 mls) and dried in vacuo (of about 30 mm Hg).

From gas chromatographic analyses, the yields of the obtained products were determined to be of follows:

3-phenoxybenzyl bromide: 54,19%

3-phenoxybenzal bromide: 44,09%

3-phenoxytoluene: 1,00%

3-phenoxybenzyl tribromide: 0,57%

(the analyses of the filtrate were by gas chromatography using a column of 2 mm internal diameter and 1 m length, filled with 3% OV17 on Gaschrom Q, temperature 100–250 degress Celsius, at a rate of 15 degress per minute).

EXAMPLE 2

An amount of 600 g of m-phenoxytoluene (produced by Fluka) was introduced into a three necked flask, equipped with a stirrer and a reflux condenser. Into the same flask the following reagents were introduced:
807 g of 1,3-dibromodimethylhydantoin
42 g of azo-iso-butyronitrile, and
1600 ml of carbontetrachloride.
The mixture was treated as in Example 1, resulting in the following yields of the products:
3-phenoxybenzylbromide: 46.52%
3-phenoxybenzalbromide: 48.03%
3-phenoxytoluene: 0.45%, and
3-phenoxybenzyldibromide: 1.30%.

The filtered out solid consisted of 358 g of dimethylhydantoin which represented a recovery of 98.3% from the used brominating agent.

EXAMPLE 3

The procedure as described above was repeated using the following reagents:
300 g m-phenoxytoluene.
403.5 g dibromodimethylhydantoin.
21 g azo-iso-butyronitrile.
2700 mls chlorobenzene.

The mixture was fast heated to boiling temperature (122 degrees centigrade) and kept at this temperature for about ten minutes.

The filtrate was analyzed by gas chromatography and the compositions were found to be as follows:
m-phenoxybenzylbromide: 38.92%
m-phenoxybenzalbromide: 59.73%
3-phenoxytoluene: 0.23%
3-phenoxybenzyltribromide: 1.11%

EXAMPLE 4 (continuous experiment)

A slurry was prepared consisting of the following constituents:
1500 g of 3-phenoxytoluene
2107 g of 1,3-dibromodimethylhydantoin
157.5 g of azoisobutyronitrile, and
8500 cc of tetrachloroethylene.

The slurry was stirred and continuously fed at the rate of 8000 ml/h into a 5 l stirred flask, equipped with a condenser and a thermomether. After an amount of about 2500 ml accumulated into the flask, it was heated to about 117±3 degrees Celsius. This temperature was kept during the entire experiment.

An orange solution was continuously pumped out from the flask so that the liquid was kept in the flask at a constant level. Samples were collected at various intervals and the results of their analyses, as determined by gas chromatography (same Column as described in Example 1) are summarized in the following Table 1.

TABLE 1

Results on a continuous experiment for the manufacture of a mixture of 3-phenoxybenzylbromide and 3-phenoxybenzalbromide.

| Collection Time (mins) | Yield % | | | |
|---|---|---|---|---|
| | m-PHT | PBZYB | PBZAB | m-PHT-Br$_3$ |
| 7–20 | 9.68 | 34.32 | 54.79 | 1.04 |
| 20–23 | 9.86 | 32.41 | 55.50 | 2.08 |
| 23–49 | 9.99 | 32.19 | 53.69 | 2.29 |
| 49–59 | 11.77 | 33.00 | 51.96 | 3.13 |
| 59–64 | 11.32 | 33.50 | 51.89 | 3.16 |
| 64–74 | 11.73 | 33.96 | 51.14 | 3.20 |
| Content of the flasks at the end | 11.36 | 35.27 | 50.12 | 3.13 |

(m-PHT = 3-phenoxytoluene;
PBZYB = 3-phenoxybenzyl bromide;
PBZAB = 3-phenoxybenzal bromide;
M—PHT—Br$_3$ = tribromophenoxy derivative).

As appears from the Table 1, even after less than 20 minutes the yield of the desired mixture was above 90%.

EXAMPLE 5 (for comparison purpose)

An experiment was performed at 64 degrees centigrade and is presented in order to illustrate the importance of the temperature parameter and does not represent the present invention.

The procedure as in Example 1 was repeated, using the following reagents:
60 g m-phenoxytoluene
97.8 g dibromodimethylhydantoin
4.2 g azoisobutyronitrile, and
600 ml of tetrachloroethylene.

The mixture was heated at 64 degrees and kept at this temperature for about 209 minutes. The filtrate was analyzed by gas chromatography and the compositions of the constituents were as follows:
m-phenoxytoluene: 59.5%
m-phenoxybenzylbromide: 27.36%
6-phenoxytoluene(6-Br-mPHT): 13.12%

The large amount of by-product (6-Br-mPHT) as well as of the starting m-phenoxytoluene, rendered the product as completely unsuitable for the production of synthetic pyrethroid-type insecticides.

EXAMPLE 6

An amount of 15 g m-phenoxytoluene and 60 ml tetrachloroethylene were introduced in a 500 ml flask equipped with a condenser, a stirrer and a thermomometer. The mixture was brought to boiling at about 121 degrees centigrade. After adding 0.035 g AIBN to the boiling solution, a slurry containing 20 g dibromodimethylhydantoin and 0.315 g azoisobutyronitrile in 75 ml of tetrachloroethylene was continuously fed into the reactor for about nine minutes. The reaction mixture was cooled to the ambient temperature and the solid material filtered off to yield after evaporation of the solvent a product with the following composition:

| | analysed by gas chromatography | analysed by NMR* |
|---|---|---|
| m-phenoxytoluene | 0.8 | 0.8 |
| m-phenoxybenzyl bromide | 42.8 | 43.2 |
| m-phenoxy benzal bromide | 54.7 | 57.1 |
| m-phenoxy benzyl tribromide | 0.9 | —** |

*Comparison to tetrachloroethane which was added to the sample to be analyzed.
**Could not be calculated.

What is claimed is:

1. A process for the manufacture of a mixture of 3-phenoxybenzyl bromide and 3-phenoxybenzal bromide, comprising the step of brominating 3-phenoxytoluene using dibromodimethylhydantoin as a brominating agent in the presence of radical initiators, wherein the bromination step is carried out in a non-polar inert solvent, at a temperature above 65 degrees Celsius using a molar ratio of the dibromodimethylhydantoin and 3-phenoxy-toluene in the range of 0.5:1 to 1.25:1 sufficient such that said mixture of 3-phenoxybenzyl bromide and said 3-phenoxybenzal bromide is substantially free of ring brominated compounds.

2. A process according to claim 1, wherein the radical initiators are selected from the groups consisting of ultraviolet rays and compounds containing azo-groups, peroxides, or mixtures thereof.

3. A process according to claim 2, wherein said compounds are selected from azo-bis-iso-butyronitrile and benzoyl peroxide.

4. A process according to claim 1, wherein the amount of free radical initiator is in the range of between 1 to 100 parts by weight per 100 parts of 3-phenoxytoluene.

5. A process according to claim 3, wherein the amount of free radical initiator is in the range of 1 to 10 parts by weight per 100 parts of 3-phenoxytoluene.

6. A process according to claim 1, wherein said bromination is carried out by gradual addition of dibromodimethylhydrantoin and radical initiator.

7. A process according to claim 1, wherein said non-polar solvent is selected from dibromoethane, dichloroethane, tetrachloroethane, tetrachloroethylene, tetrachloromethane and chlorobenzene.

8. A process according to claim 7, wherein the amount of said non-polar solvent is in the range of between 50% to 90% by volume of the reactants.

9. A process according to claim 1, wherein said bromination is carried out in a continuous manner.

10. A process according to claim 9, wherein about 10% of the radical initiator is introduced from the beginning into the reaction mixture.

11. A process according to claim 1, wherein the temperature of the reaction is about the boiling point of the non-polar solvent utilized in the process.

* * * * *